United States Patent [19]

Stevens

[11] Patent Number: 5,783,440
[45] Date of Patent: Jul. 21, 1998

[54] CULTURE VESSEL

[75] Inventor: Timothy A. Stevens, Warwick, N.Y.

[73] Assignee: Becton Dickinson and Company, Franklin Lakes, N.J.

[21] Appl. No.: 719,827

[22] Filed: Sep. 30, 1996

[51] Int. Cl.[6] .................................................. C12M 1/24
[52] U.S. Cl. ............................ 435/304.3; 435/304.1; 435/304.2; 422/102; 215/40; 215/386; 220/731
[58] Field of Search ........................... 435/288.1, 288.2, 435/304.1, 304.2, 304.3; 215/40, 41, 386, 400; 422/102; 220/719, 731

[56] References Cited

U.S. PATENT DOCUMENTS

| 2,947,116 | 8/1960 | Earle et al. | 435/304.3 |
|---|---|---|---|
| 3,451,894 | 6/1969 | Anandam | 435/304.2 |
| 3,616,263 | 10/1971 | Anandam | 435/304.2 |
| 3,870,602 | 3/1975 | Froman et al. | 435/304.3 |
| 4,073,695 | 2/1978 | Lyman | 435/304.3 |
| 4,334,028 | 6/1982 | Carver | 435/284 |
| 4,665,035 | 5/1987 | Tunac | 435/304.2 |
| 4,770,854 | 9/1988 | Lyman | 422/102 |
| 5,202,093 | 4/1993 | Cloyd | 435/304.1 |
| 5,358,872 | 10/1994 | Mussi et al. | 435/296 |

*Primary Examiner*—William H. Beisner
*Attorney, Agent, or Firm*—Bruce S. Weintraub; Nanette S. Thomas

[57] ABSTRACT

A vessel assembly for culturing cells wherein a breaker wall zone is provided in the opening of the vessel to minimize media beach or travel into the neck from the vessel body.

4 Claims, 9 Drawing Sheets

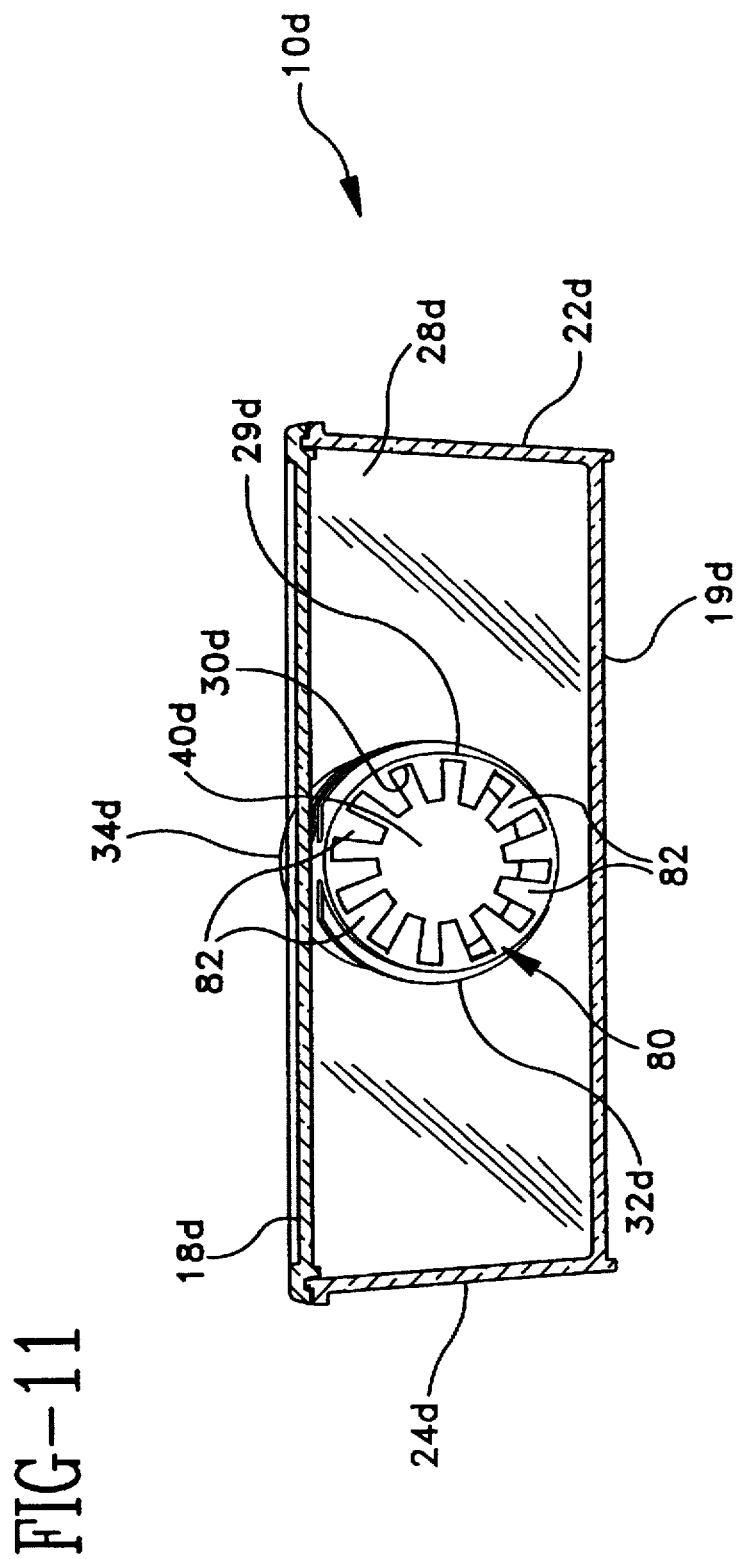

3,783,440

CULTURE VESSEL

BACKGROUND OF THE INVENTION

1. Field of the Invention

The present invention relates to a device for cell and/or tissue culture production, and more particularly to a vessel having means for minimizing the beaching of media back into the neck of the vessel which results in improved methods for growing cells, tissues and microorganisms.

2. Description of the Related Art

Tissue culture flasks are used in the laboratory for many purposes. Typically, these flasks are used to culture microorganisms or tissues in a culture medium or agar which is adhered to an interior surface of the flask.

In use, tissue culture flasks have a neck or opening at one end of the flask permitting access to the interior of the flask. The flask may be filled with culture medium and tissue to a level approaching the bottom of the neck or opening. The medium and tissues are introduced into the flask through a capped opening. Therefore, during handling, media tends to beach or travel into the neck, possibly contacting the closure, which may contaminate the media and cells.

A special need exists for an improved tissue flask which (1) provides a means between the neck and flask body for minimizing media beaching into the neck (2) provides pipet or scraper access into the flask and (3) provides access to media as well as pouring of cells out of the flask without interference.

It is therefore desirable to provide a tissue culture flask having a sufficiently large opening so as to permit access to the entire bottom surface thereof without decreasing the usable volume, minimizes media beaching into the neck from the flask body and minimizes interference with the pouring of cells out of the flask.

SUMMARY OF THE INVENTION

The present invention is a vessel comprising a chamber, an opening in the chamber, a closure or other means associated with the opening, a neck between said chamber and said opening and means associated with said opening for minimizing media beach or liquid travel into the neck.

The vessel preferably includes a chamber having a generally flat bottom wall, upwardly extending front, back and lateral walls bounding the bottom wall, and an upper, generally planar cover surface which is parallel to the bottom wall to enclose the chamber and define a chamber interior.

Preferably, the vessel is a flask or roller bottle. Most preferably, the vessel is a flask.

Most preferably, the means to minimize media beach or liquid travel into the neck from the chamber body is a breaker wall zone. The breaker wall zone provides a reduction in the opening between the chamber and the neck. The breaker wall zone minimizes the travel back of media from the chamber interior to the closure without restricting access to the chamber interior or decreasing the usable volume of the vessel or interfering with the pouring of cells out of the vessel.

DESCRIPTION OF THE DRAWINGS

FIG. 11 is a side elevational view of the flask of FIG. 10 taken along line 11—11 thereof, partially in section of the breaker wall zone.

DETAILED DESCRIPTION

Figure 1:
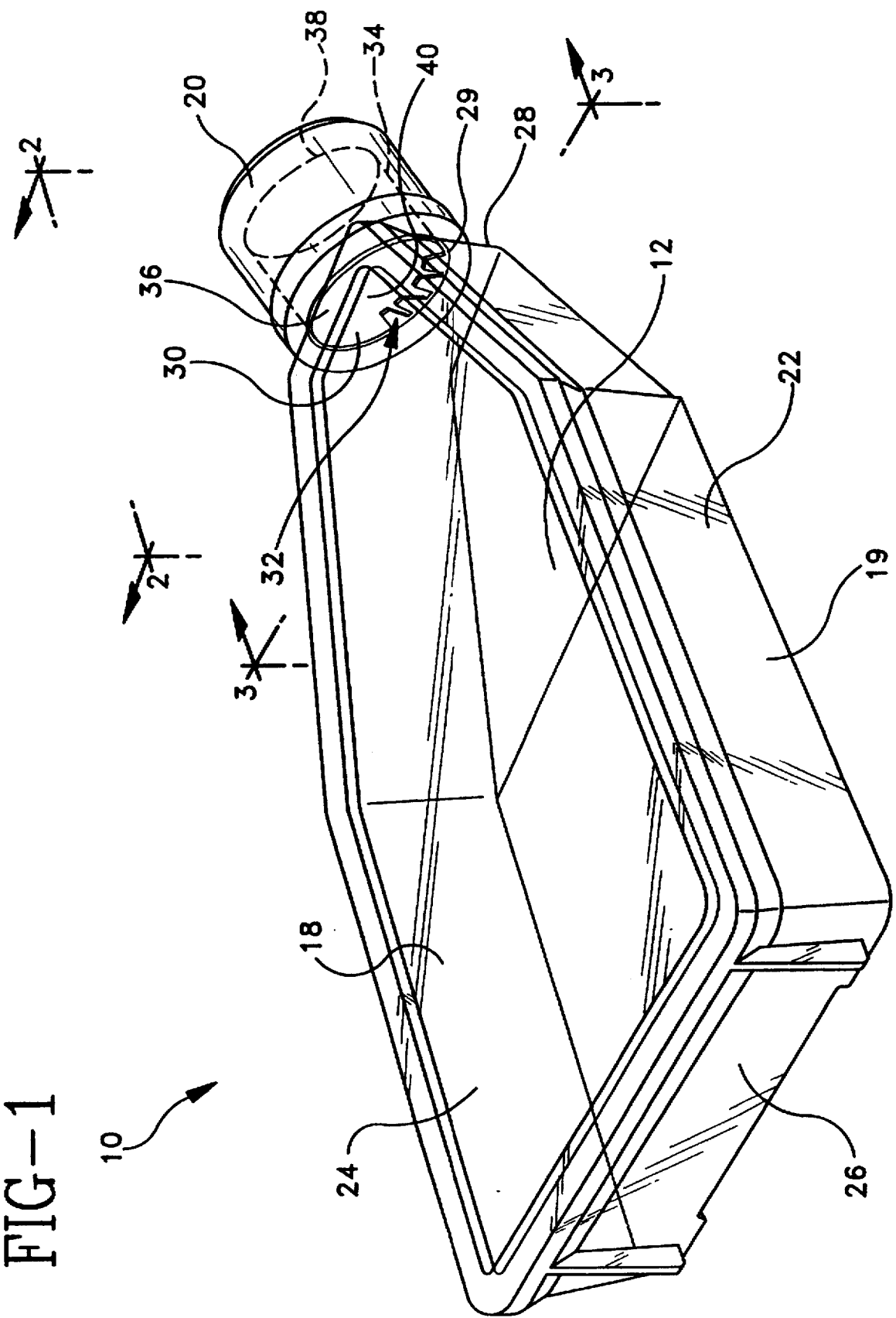
FIG. 1 is a perspective view of a flask with a breaker wall zone.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

FIG. 1 illustrates a cell culturing vessel 10. Cell culturing vessel 10 includes a body 12 and a cap 20. The body is preferably made from impact resistant plastic or glass which is gas impermeable, optically clear, non-toxic and inert with respect to the cells to be cultured.

The body of the vessel holds material that is adapted to be held until such time as the same is withdrawn or dispensed. It is unimportant whether body 12 has a particular geometric configuration.

Figure 2:
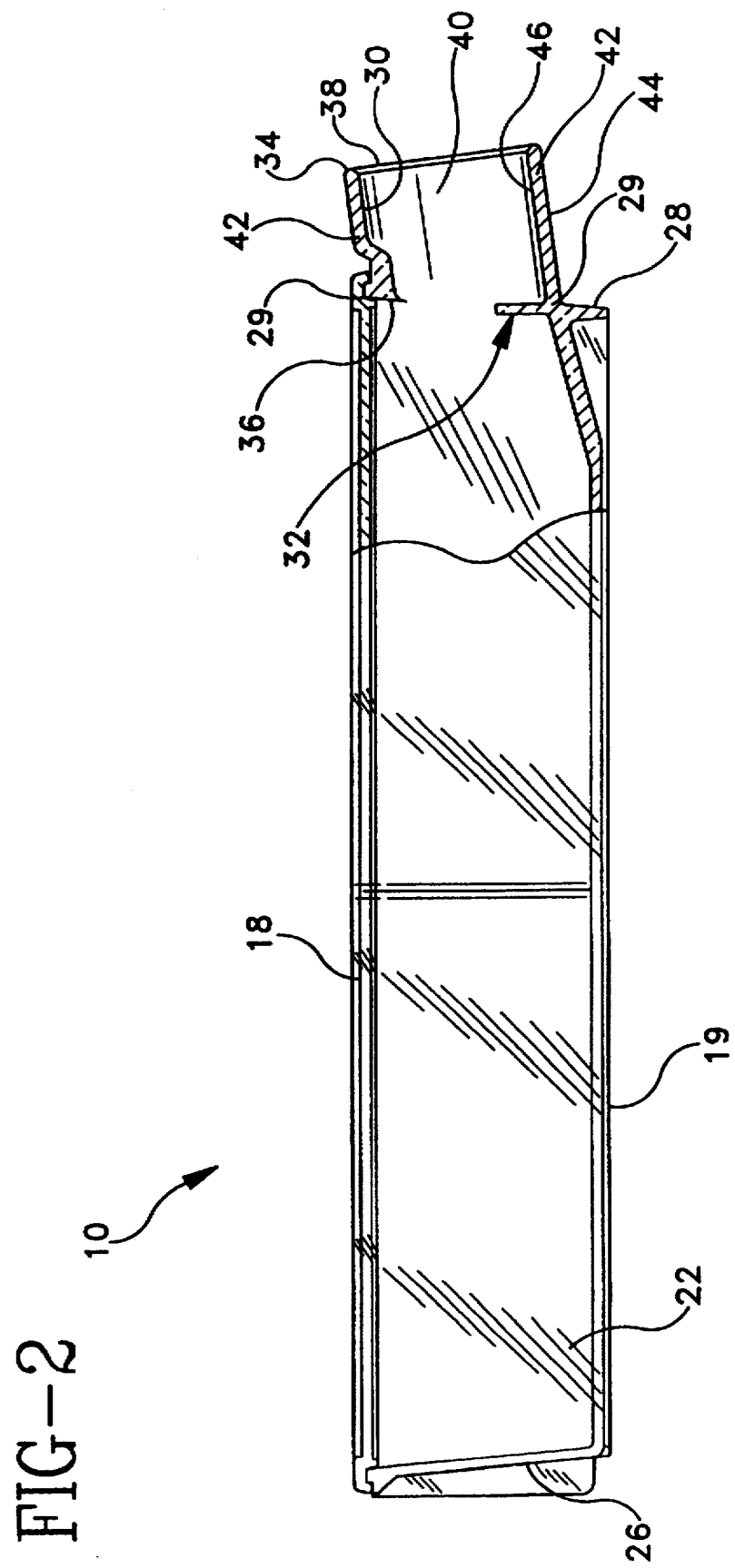
FIG. 2 is a side elevational view of the flask of FIG. 1 taken along line 2—2 thereof, partially in section of the breaker wall zone.
Figure 3:
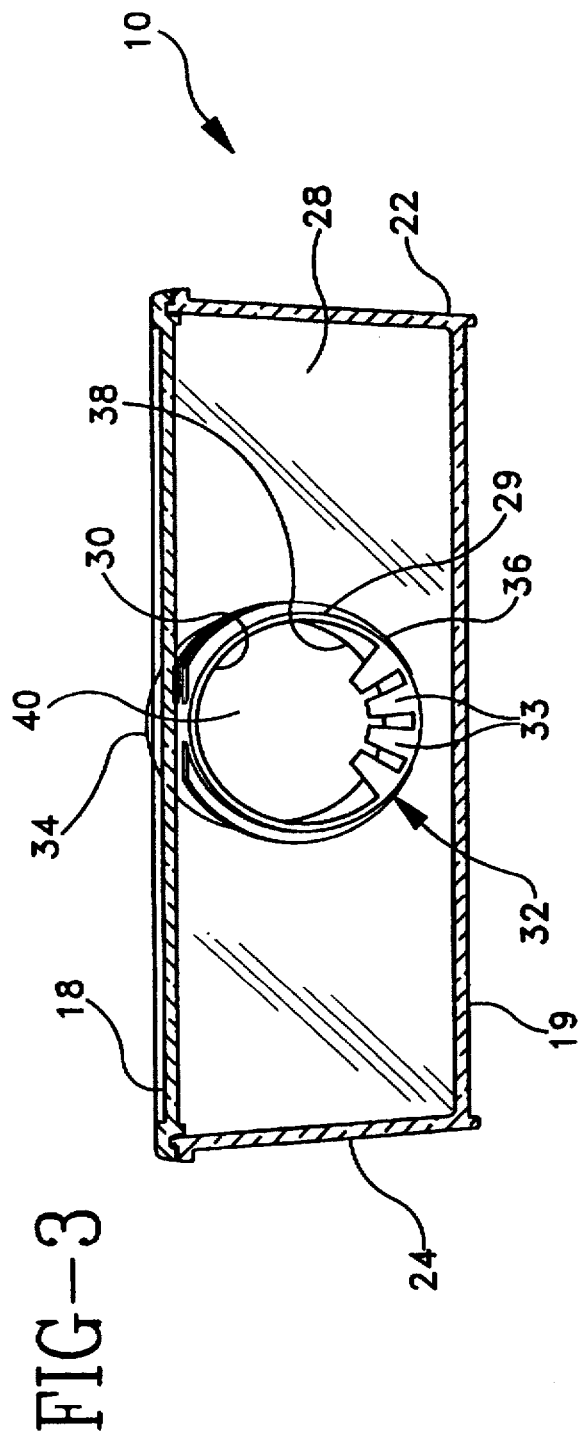
FIG. 3 is a longitudinal cross section of the flask of FIG. 1 taken along line 3—3 thereof.

As shown in FIGS. 1 and 2, body 12 includes a top wall area 18, a bottom wall area 19 and a pair of similar or lateral side walls 22 and 24. A back closed end wall 26 is provided as well as a front end wall 28. A neck 34 extends from front end wall 28 wherein there is an interface area 29 between neck 34 and front end wall 28. As shown in FIGS. 2 and 3, front end wall 28 has an opening 30 and interface area 29 between front end wall 28 and neck 34 includes a breaker wall zone 32. Breaker wall zone includes protrusions or tabs 33 that can be of any desirable geometric configuration or size so as to minimize media beach or liquid travel into the neck while minimizing interference with access to the interior of the vessel.

As shown in FIG. 3, to permit access to the interior of body 12, front end wall 28 includes a general circular opening 30 and an extending neck 34. Neck 34 is generally a uniformly cylindrical member having a first end 36 supported on front end wall 28 of opening 30. Interface area 29 between first end 36 and front end wall 28 is where breaker wall zone 32 is located. Neck 34 includes an open second end 38 opposite first end 36 and defines a central bone or passage 40 between the ends and in communication with the interior of flask 12 through opening 30. Central bone 40 is defined by a cylindrical wall 42. Cylindrical wall 42 includes an outer wall surface 44, which may be externally screw-threaded so as to accommodate a conventional, internally threaded screw cap 20 for closing bore 40 and sealing the interior of body 12 and an inner wall surface 46.

The culture medium which supports the growth of the tissues typically covers the entire main planar portion of bottom wall 19. The medium may be filled in body 12 to such a level that it begins to rise to opening 30. Thus, it can be appreciated that to reduce or minimize media or liquid from exiting opening 30 through neck 34 breaker wall zone 32 is very effective.

Breaker wall zone 32 may be formed in a variety of ways, including but not limited to a molding operation or through a milling, cutting or other thickness reduction mechanism, all as is known in the art.

Figure 4:
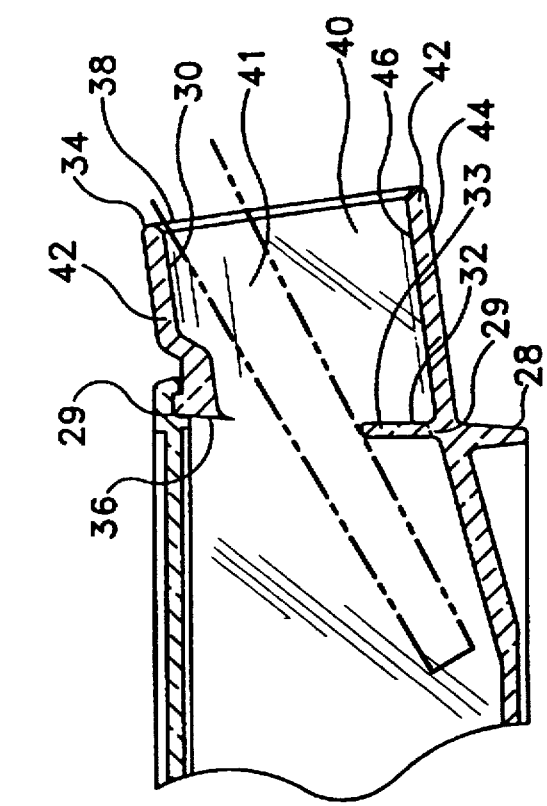
FIG. 4 illustrates the present invention of FIG. 1 in use.

In use, a pipet or scraper 41 could easily extend over and beyond the breaker wall zone as shown in FIG. 4.

Figure 5:
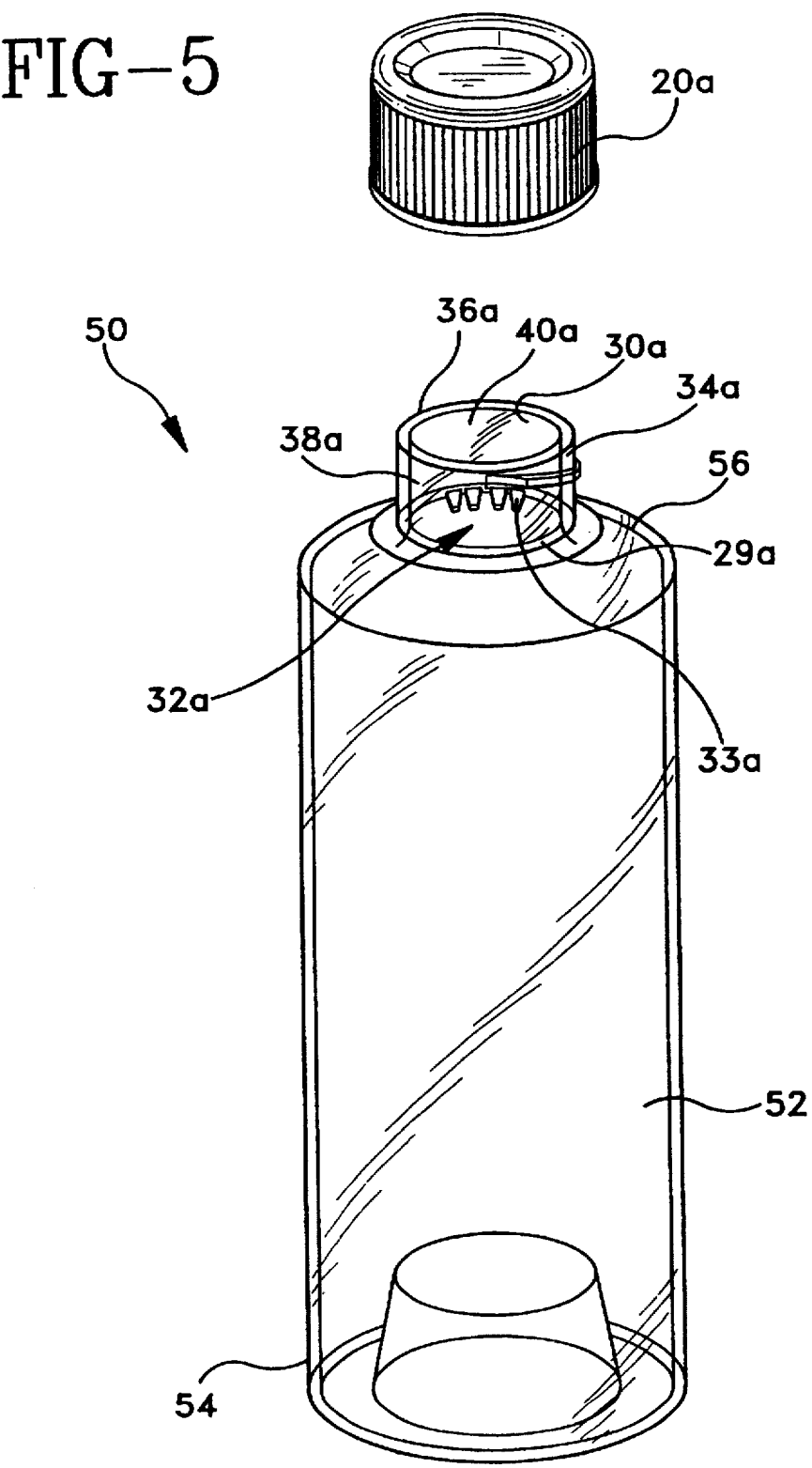
FIG. 5 is an alternate embodiment of the invention illustrating a perspective view of a roller bottle with a breaker wall zone.

The invention, as shown in FIG. 5 includes many components which are substantially identical to the components of FIGS. 1–3. Accordingly, similar components performing similar functions will be numbered identically to those components of FIGS. 1–3, except that a suffix "a" will be used to identify those similar components in FIG. 5.

The applicability of a breaker wall zone to culture vessels other than flask 12 as shown in FIG. 1 is shown in FIG. 5. Roller bottle 50 as shown in FIG. 4 is an alternate embodiment of a culture vessel that has a breaker wall zone 32a. Roller bottle 50 includes a cylindrical body 52 extending from a bottom portion 54 to a top portion 56. Top portion 56 has an opening 30a that includes breaker wall zone 32a.

Figure 6:
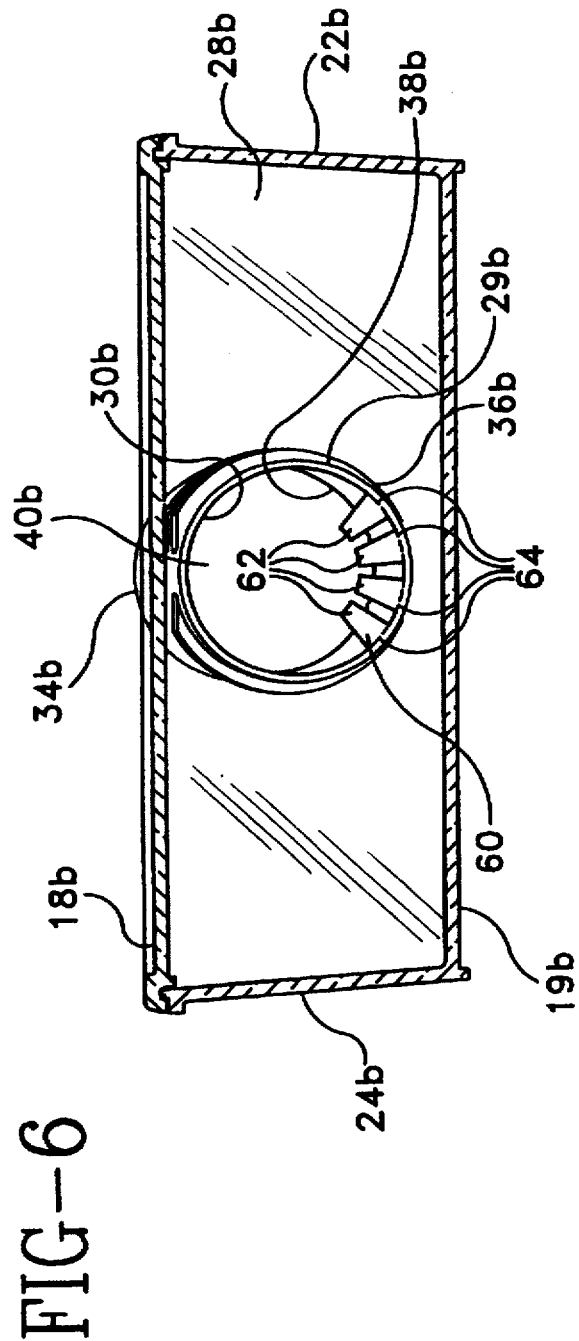
FIG. 6 is an alternate embodiment of the invention illustrating an alternate breaker wall zone in a flask.
Figure 7:
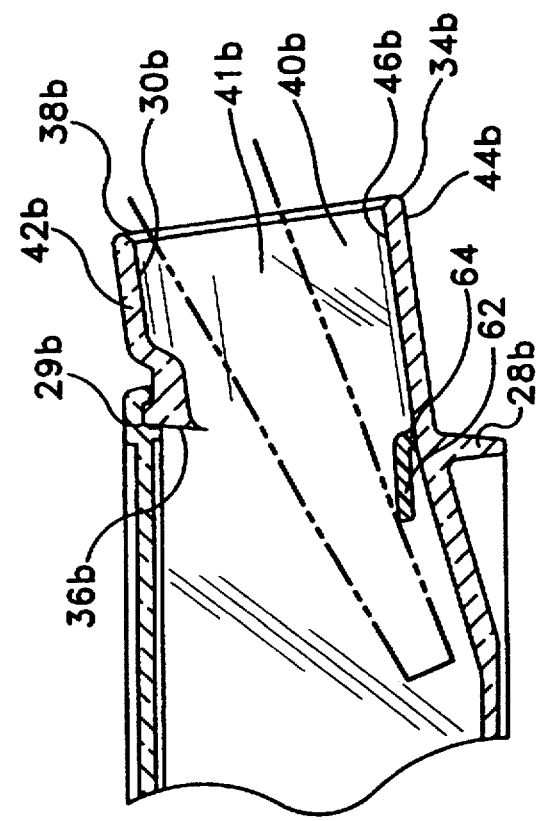
FIG. 7 illustrates the alternate embodiment of the present invention of FIG. 6 in use.

The invention, as shown in FIGS. 6–7 includes many components which are substantially identical to the components of FIGS. 1–3. Accordingly, similar components performing similar functions will be numbered identically to those components of FIGS. 1–3, except that a suffix "b" will be used to identify those similar components in FIGS. 6–7.

As shown in FIGS. 6–7, a breaker wall zone 60 having tabs 62 is removably attached to opening 30b. A perforated section 64 provides the means for removing the breaker wall zone from the vessel. Perforated section 64 is located between breaker wall zone 60 and opening 30b of the vessel or at the interface area 29b between neck 34b and front end wall 28b.

Most preferably, the removably attached breaker wall zone is made of light weight material including but not limited to paper or plastic such as mylar so long as the paper or plastic material is inert to the media, liquids, cells or tissues associated with the process of using the vessel.

The light weight material of the breaker wall zone provides full access into the vessel with minimal restriction because the zone is not rigid but somewhat flexible. Therefore, in use, a pipet or scraper 41b could easily extend over and beyond the breaker wall zone as shown in FIG. 7. The breaker wall zone easily moves out of the way of the pipet or scraper. Then once the pipet or scrapper is removed from the vessel, the breaker wall zone returns to its original position so as to minimize media beaching or liquid travel into the neck. It may also be desirable to the user to remove the breaker wall zone from the vessel at the perforated section at a time appropriate and/or convenient to the user.

Figure 8:
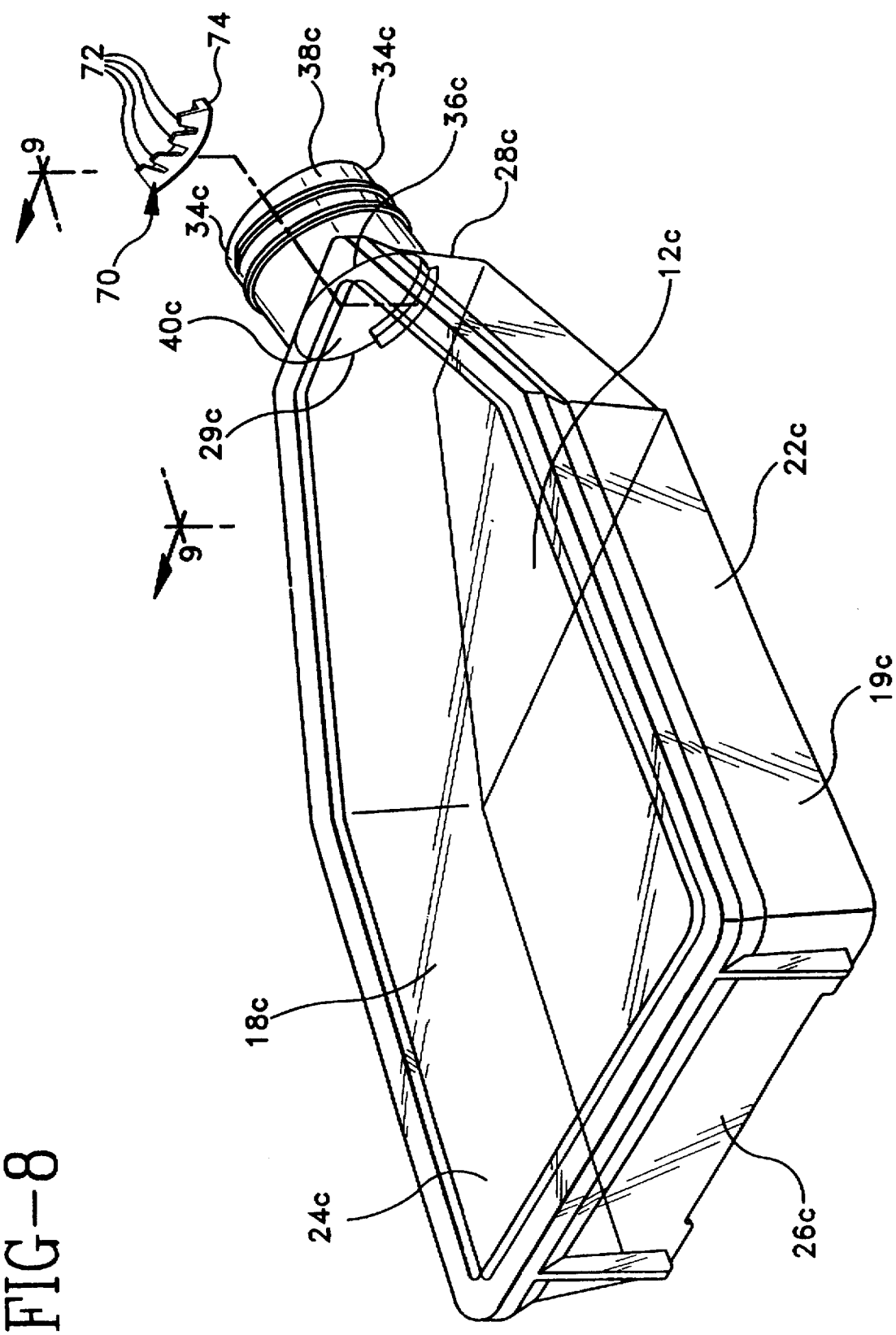
FIG. 8 is an alternate embodiment of the invention illustrating an alternate breaker wall zone in a flask.
Figure 9:
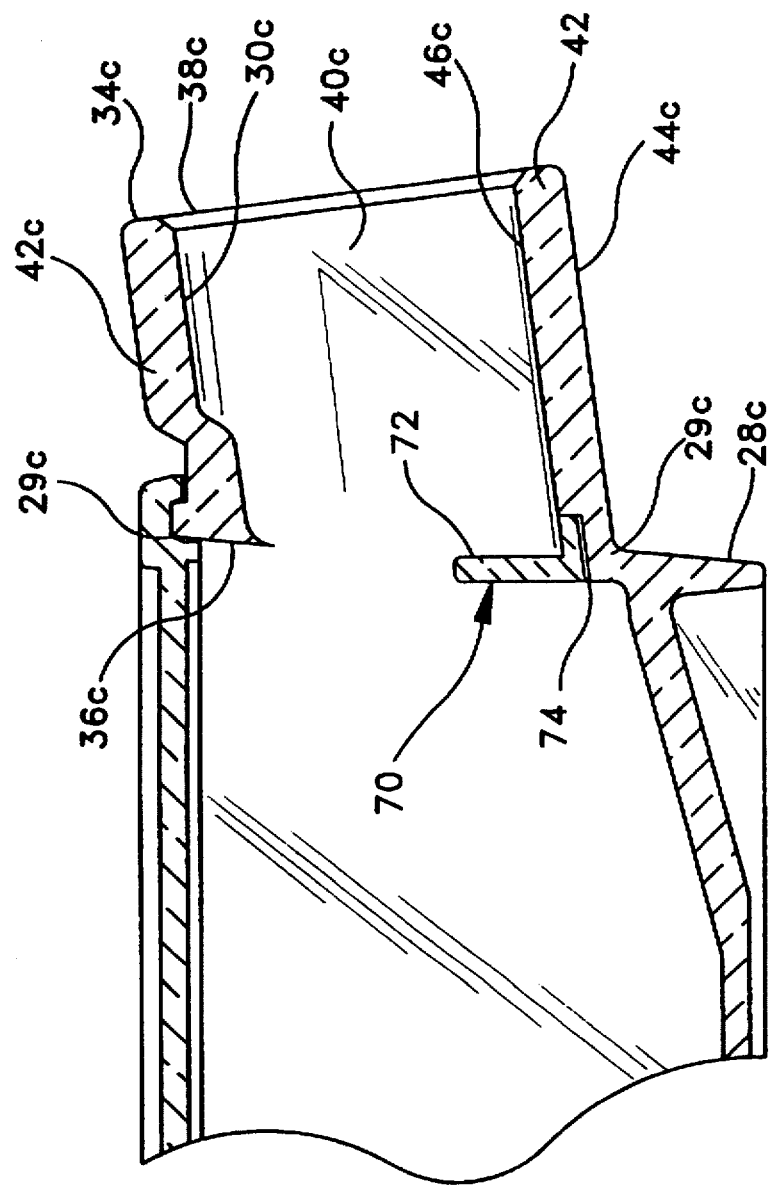
FIG. 9 is a side elevational view of the flask of FIG. 8 taken along line 9—9 thereof, partially in section of the breaker wall zone.

The invention, as shown in FIGS. 8–9, includes many components which are substantially identical to the components of FIGS. 1–3. Accordingly, similar components performing similar functions will be numbered identically to those components of FIGS. 1–3, except that a suffix "c" will be used to identify those similar components in FIGS. 8–9.

An alternate embodiment of the invention is shown in FIGS. 8–9 wherein the means for removably attaching the breaker wall zone 70 with tabs 72 to the interface area 29c between neck 34c and front end wall 28c is an adhesive material 74. The adhesive material does not provide a permanent bond so that the breaker wall zone may be removed and reattached to the vessel.

Most preferably, the removably attached breaker wall zone is made of light weight material including but not limited to paper or plastic such as mylar so long as the paper or plastic material is inert to the media, liquids, cells or tissues associated with the process of using the vessel.

Figure 10:
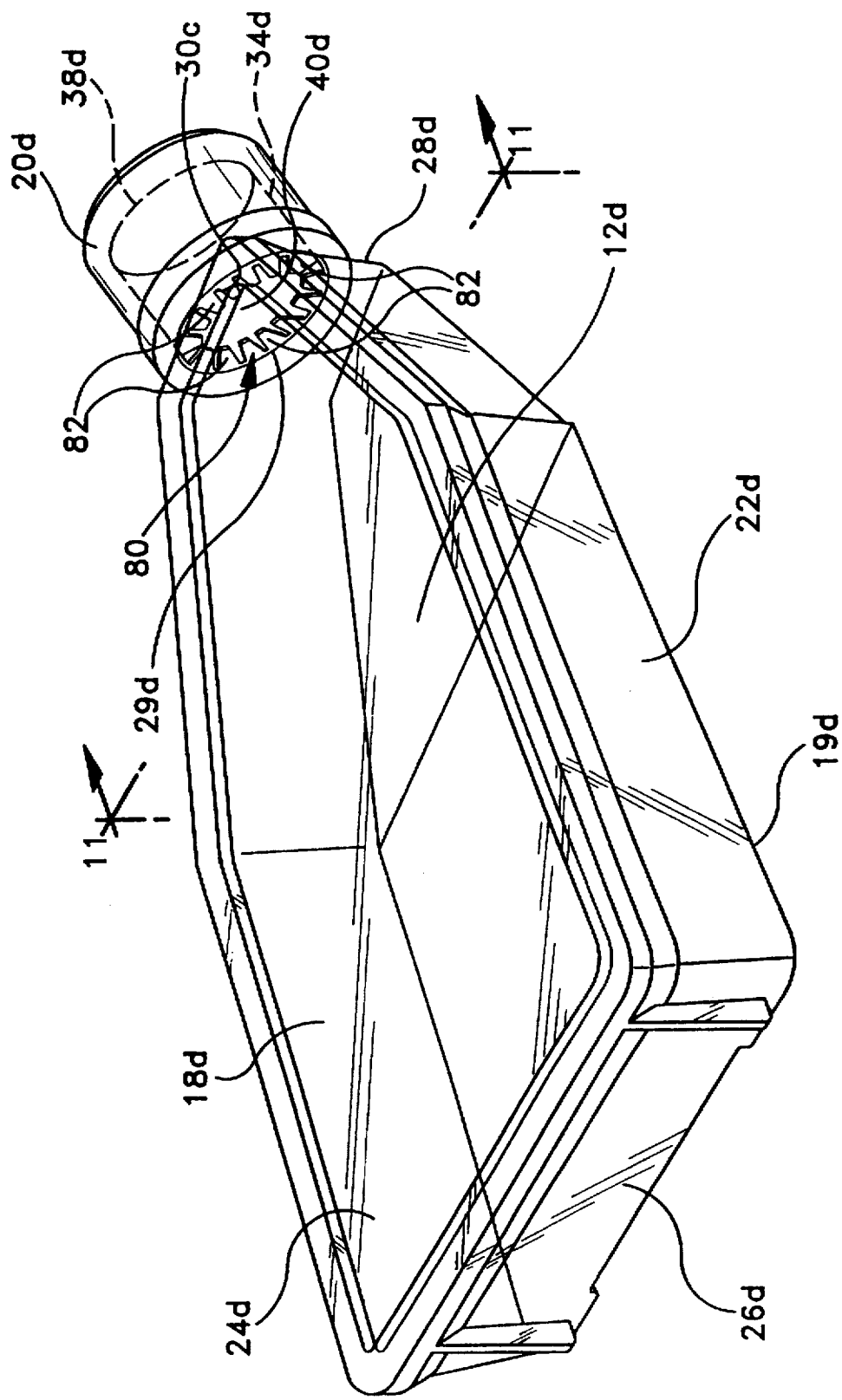
FIG. 10 is an alternate embodiment of the invention illustrating an alternate breaker wall zone in a flask.

The invention, as shown in FIGS. 10–11, includes many components which are substantially identical to the components of FIGS. 1–3. Accordingly, similar components performing similar functions will be numbered identically to those components of FIGS. 1–3, except that a suffix "d" will be used to identify those similar components in FIGS. 10–11.

An alternate embodiment of the invention is shown in FIGS. 10–11 wherein the breaker wall zone 80 with tabs 82 extends around the entire circumference of opening 30d of the vessel at the interface area 29d between neck 34d and front end wall 28d. Breaker wall zone may be formed in a variety of ways, including but not limited to a molding operation or through a milling, cutting or other thickness reduction mechanism, all as is well known in the art. An example of the particular formulation is similar to that shown in FIG. 3 above. In addition, breaker wall zone may be removably attached to interface area 29d by a perforated section or by an adhesive material. Furthermore, breaker wall zone 80 may be made of light weight material including but not limited to paper or plastic such as mylar so long as the paper or plastic material is inert to the media, liquids, cells or tissues associated with the process of using the vessel.

What is claimed is:

1. A vessel comprising:

a body having a generally flat bottom wall, upwardly extending front, back and lateral walls bounding said bottom wall, and an upper, generally planar cover surface that is parallel to said bottom wall;

a generally circular opening in said front wall;

a neck extending from said opening in said front wall, said neck having inner and outer cylindrical walls;

an interface area between said neck and said opening in said front wall; and means for minimizing media beaching or liquid travel into said neck from said body located at said interface area, wherein said means for minimizing beaching is a breaker wall zone.

2. The vessel of claim 1 further including a cap.

3. The vessel of claim 2 wherein said breaker wall zone is removably attached to said interface area.

4. The vessel of claim 3 wherein said breaker wall zone is made of paper or plastic.

* * * * *